April 25, 1972 J. M. GARABEDIAN Plant Pat. 3,133
NECTARINE TREE
Filed June 19, 1970
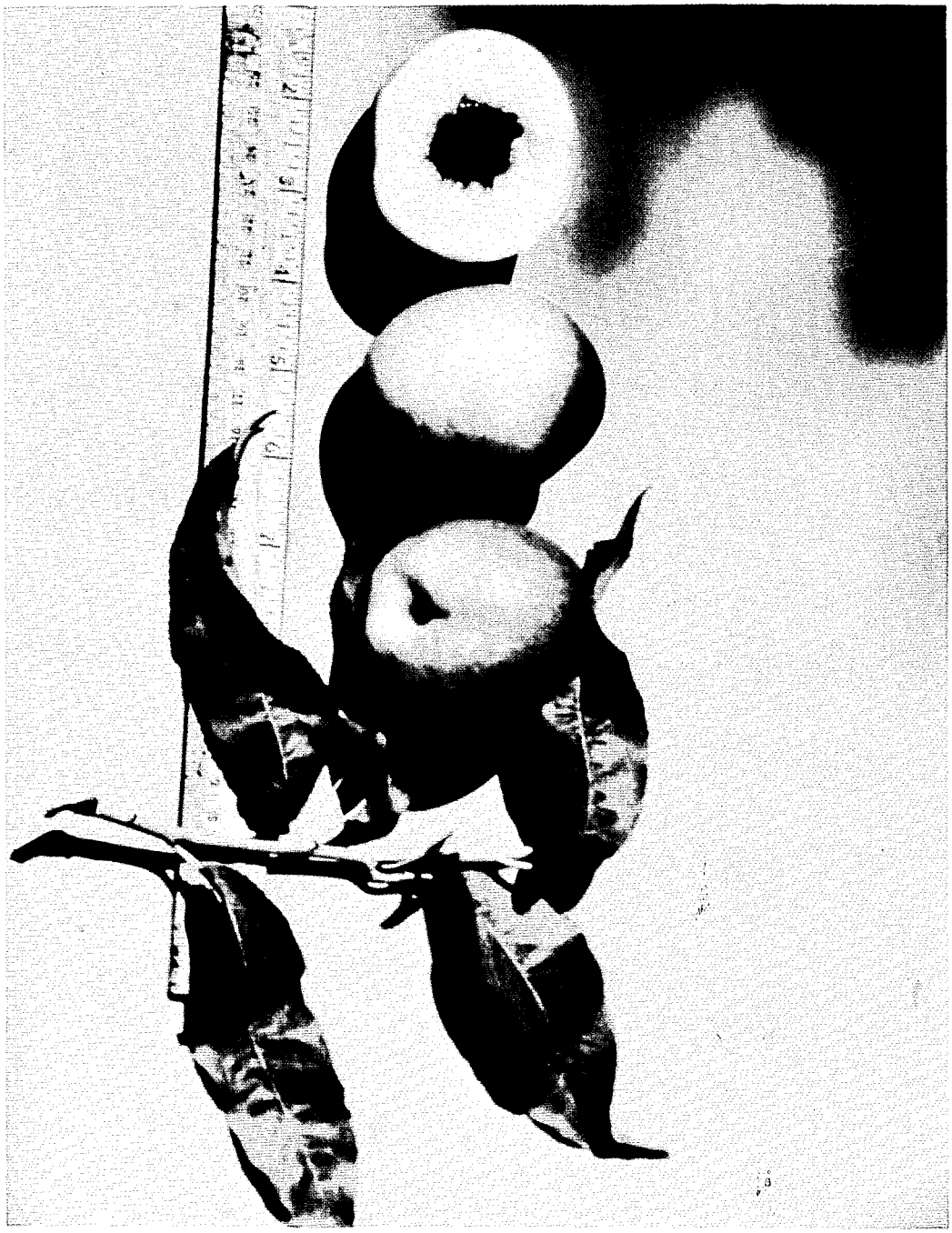
JOHN M. GARABEDIAN
INVENTOR
Hueber & Worrel
ATTORNEYS

United States Patent Office

Plant Pat. 3,133
Patented Apr. 25, 1972

3,133

NECTARINE TREE

John M. Garabedian, 3158 Hamilton St., Fresno, Calif. 93712

Filed June 19, 1970, Ser. No. 47,813
Int. Cl. A01h *5/03*
U.S. Cl. Plt.—41 1 Claim

The present invention relates to a nectarine tree and more particularly to a new and distinct variety thereof broadly characterized by its substantially upright, spreading form; vigorous and regular bearing; early bloom; and the production of early ripening, highly colored, freestone, firmly textured, yellow-fleshed fruit having yellow, red-blushed skin.

Thes instant variety nectarine tree blooms relatively early as compared with most other early nectarine varieties, approximately seven days earlier than the Regular Le Grand (unpatented) nectarine tree which it most nearly resembles. The fruit of the new variety, however, distinguishes from the Regular Le Grand by ripening somewhat earlier and having a more intense, highly colored skin. The fruit of the subject variety is also larger, more nearly spherical, and the flesh is much firmer and more highly colored than the fruit of the Regular Le Grand. The flavor of the fruit of the new variety is somewhat similar to the fruit of the Elberta (unpatented) peach tree.

I originated the present variety of nectarine tree on my ranch on Church Avenue, between Peach and Willow Avenues, near Fresno, Calif. Seeds were gathered from the fruit of the June Belle nectarine tree of U.S. Plant Patent No. 2,323 growing in an orchard on my above designated ranch in June 1962. The seeds resulted from chance pollination of the blossoms of the June Belle. The seeds were placed in cold storage until planted in a bottom heated hothouse in October of the same year. The seeds produced a number of seedling nectarine trees which were transplanted on my above designated ranch in nursery rows in March 1963. In 1965, the seedling trees fruited sufficiently to permit the selection of one of the seedling trees as the subject variety which exhibited the above discussed distinctive and highly desirable characteristics. The seedling was asexually reproduced in 1966 by fall dormant budding of scions therefrom on a number of Nemaguard (unpatented) rootstocks in an orchard at my No. "41" ranch on the northeast corner between Road 41 and Avenue 12 in Madera County, Calif. The trees resulting from the budded rootstock fruited in July 1968 and the fruit and tree characteristics thereof proved identical to those of the original seedling tree.

The accompanying drawing is a dye transfer color print of a photograph showing the leaves and several mature fruit of the subject variety with one of the fruit divided in a plane right-angularly related to its suture plane to reveal flesh coloration and pit characteristics.

Referring more specifically to the pomological details of this new and distinct variety of nectarine tree, the following characteristics have been observed under the ecological conditions prevailing at my ranch in Madera County, State of California. All major color plate identifications are by reference to the Maerz and Paul Dictionary of Color.

*Tree*

Size: Medium, substantially upright but spreading and open with density determnied by pruning methods; hardy, very productive and regular bearer.

Trunk: Generally smooth.

Branches: Medium smooth; current season's dorsal growth being a light green (18–I–5) while the ventral growth is somewhat rose colored (5–I–1) over green in many areas with a slight tinge of red near the tip; two year old branches being dark brownish gray (8–C–9) to dark brown (15–C–10). *Lenticels*—small size and average in number.

Leaves:

*Size.*—Medium to large.

*Length.*—Average 5⅝".

*Width.*—Average 1⅝".

*Shape.*—Lanceolate, glabrous, acuminate at apex, medium thickness, distinctively wavy and crinkled along midrib.

*Color.*—Dorsal surface, Mt. Vernon green (23–H–8). Ventral surface, spinach green (22–K–7).

*Marginal form.*—Glandular, crenate, base broadly acute with leaf pinnately veined.

*Midrib color.*—Ventral surface, chartreuse yellow (11–H–1).

*Glands.*—Generally globose, usually opposite with few alternating on petiole near blade base, mostly green with red apex.

*Petiole.*—Medium length, averaging 7/16", generally slender, averaging 1/16", dorsal surface, piquant green (20–K–6), ventral surface chryolite green (19–K–3).

*Stipules.*—None.

*Leaf buds.*—Medium size, pointed to round.

Flower buds: Hardy, generally large, plumb, free and pubescent.

Flowers: First bloom approximately March 3 with full bloom occurring approximately March 18; relatively large, average spread 41 mm. Color.—Cameo pink (50–C–2) to (50–H–2); inside color of calyx cup mandarin orange, anthers averaging approximately 44 in number, wind flower red (53–L–1 to L–6).

*Fruit*

Maturity when described, eating hard, approximately July 11.

Size: Uniformly large, average axial diameter 2⅜", average dimension transversely in suture plane 2½".

Form: Generally uniform, somewhat unsymmetrical, substantially globose in the plane right-angularly disposed from the suture plane.

Suture. Distinct but shallow line extending from the base and somewhat beyond the apex with slight depression beyond pistil point.

*Ventral surface.*—Slightly rounded and lipped from base to apex on one side.

*Lips.*—Unequal.

*Cavity.*—Medium narrow, average ¾", relatively deep, average ¼".

*Base.*—Cunate to truncate.

*Apex.*—Generally prolonged, pistil point slightly depressed and hooked.

*Stem.*—Short to medium, average length ¼", average diameter ⅛".

Skin: Thick, tough, tenacious to flesh.

*Texture.*—Smooth with substantially no pubescence.

*Color.*—At base, under color lime yellow (11–L–5) stippled and splotched over base color with oxheart red (6–L–5), blush areas India red (7–11–6) to andorra red (8–L–4).

Flesh:

*Color.*—Jonquil yellow (9–J–5) streaked with some red next to the skin and the stone but mostly toward the apex.

*Surface of pit cavity.*—Pink to mayflower red (3–J–3).

*Juice.*—Abundant and rich.

*Texture.*—Firm, coarse and crisp.

*Fibers.*—Abundant, coarse and tender.

*Ripens.*—Generally even.

*Flavor.*—Mild and delicately vinuous, generally similar to the Elberta peach.

*Aroma.*—Wanting to very slight.

*Eating quality.*—Very good.

Stone: Generally free but occasionally adheres to the flesh upon the dorsal and ventral edges with relatively few fibers towa rd the base.

*Size.*—Generally large, average length 1½", average width 15/16", average thickness 11/16".

*Form.*—Mostly obovoid and cuneate toward the base.

*Base.*—Usually straight.

*Hilum.*—Relatively broad, oval.

*Apex.*—Generally rounded.

*Sides.*—Somewhat unequal, curved on one side.

*Surface.*—Irregularly furrowed near base, with ridges toward apex and pitted toward base.

*Ridges.*—Jagged toward base.

*Pits.*—Elongated.

*Ventral edge.*—Thick.

*Dorsal edge.*—Full with broad groove toward base.

*Color.*—Near base, rhododendron brown (54–L–5) to tawny brown at apex (13–B–10).

*Splitting tendency.*—None.

*Kernel.*—Oval with slight taste.

Use: Fresh market, dessert and culinary.

*Keeping quality.*—Good.

*Resistance to insects.*—Good.

*Resistance to disease.*—Good.

*Shipping quality.*—Good.

Although the new variety of nectarine tree possesses the described characteristics under the growing conditions prevailing in Madera County, in the central portion of the San Joaquin Valley of California where the new variety was first observed, it is to be understood that variations of the usual magnitude in such characteristics incident to differences in environment and treatment are to be expected.

Having thus described and illustrated my new variety of nectarine tree, what is claimed as new and desired to be secured by Letters Patent is:

1. A new and distinct variety of nectarine tree substantially as illustrated and described which is characterized by its vigorous growth; and its regular and heavy bearing of brilliantly colored fruit which is somewhat larger than the fruit of the Regular Le Grand nectraine tree (unpatented), which it most nearly resembles, but from which it is distinguished in that its fruit ripens somewhat earlier than the Le Grand and has a more intense highly colored skin and flesh which is more nearly similar to the flesh of the fruit of the Elberta peach tree (unpatented).

No references cited.

ROBERT E. BAGWILL, Primary Examiner